United States Patent
Baird

[11] Patent Number: 6,026,810
[45] Date of Patent: *Feb. 22, 2000

[54] ONE HAND DISCONNECTABLE DEVICE FOR ARTIFICIAL BREATHING APPARATUS TO ENDOTRACHEAL TUBE CONNECTIONS

[76] Inventor: David A. Baird, 5001 New Hudson Rd., Windsor, Ohio 44099

[*] Notice: This patent issued on a continued prosecution application filed under 37 CFR 1.53(d), and is subject to the twenty year patent term provisions of 35 U.S.C. 154(a)(2).

[21] Appl. No.: 08/902,659

[22] Filed: Jul. 30, 1997

[51] Int. Cl.$^7$ .................................................. A61M 16/00
[52] U.S. Cl. ............................... 128/207.14; 128/202.27; 128/912; 128/207.16; 285/18
[58] Field of Search .............................. 128/207.14, 912, 128/202.27, 207.15, 200.26, DIG. 26, 207.16, 911, 204.18, 205.17, 203.28, 205.24, 909; 285/342, 33, 39, 18, 16, 403; 604/54, 119

[56] References Cited

U.S. PATENT DOCUMENTS

| | | | |
|---|---|---|---|
| 4,138,146 | 2/1979 | Rumble | 285/39 |
| 4,202,330 | 5/1980 | Janabke | 128/204.18 |
| 4,676,239 | 6/1987 | Humphrey | 128/203.28 |
| 4,729,765 | 3/1988 | Eckets et al. | 604/54 |
| 4,790,832 | 12/1988 | Lopez | 128/205.24 |
| 4,823,828 | 4/1989 | McGinnis | 128/205.24 |
| 5,139,018 | 8/1992 | Brodsky et al. | 128/207.14 |
| 5,285,776 | 2/1994 | Bestrom | 128/207.14 |
| 5,315,991 | 5/1994 | Teves | 128/207.14 |
| 5,335,655 | 9/1994 | Lee | 128/207.16 |
| 5,579,762 | 12/1996 | Lee | 128/207.14 |
| 5,582,161 | 12/1996 | Lee | 128/207.14 |
| 5,582,166 | 12/1996 | Lee | 128/207.14 |
| 5,697,361 | 12/1997 | Smith | 128/204.18 |
| 5,720,282 | 2/1998 | Wright | 128/207.14 |

FOREIGN PATENT DOCUMENTS

| | | | |
|---|---|---|---|
| 216569 | 8/1958 | United Kingdom | 128/207.14 |
| 1082749 | 9/1967 | United Kingdom | 128/207.14 |

*Primary Examiner*—John G. Weiss
*Assistant Examiner*—V. Srivasrara
*Attorney, Agent, or Firm*—Fay, Sharpe, Fagan, Minnich & McKee, LLP

[57] ABSTRACT

A quick disconnect fitting, that is operable with one hand, is provided for connection of a endotracheal tube and an artificial breathing apparatus output tube. The fitting is preferably a rigid body member having a artificial breathing apparatus input member, a endotracheal output member, and a movable piston or plunger for manual extraction of the endotracheal tube from the endotracheal output member. A finger support member can be provided to grip with at least one finger to obtain additional leverage to depress the plunger with the palm of a user's hand. Fluid communication is always maintained from position 1 to position 2 were complete disconnection of the endotracheal tube is achieved.

15 Claims, 2 Drawing Sheets

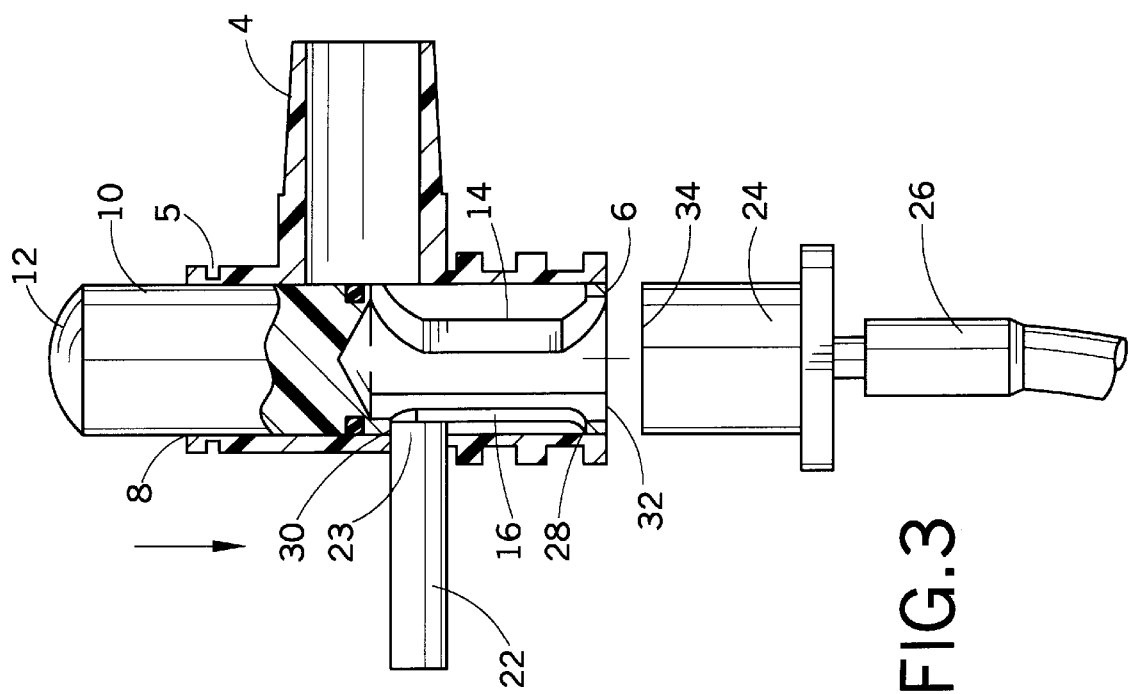
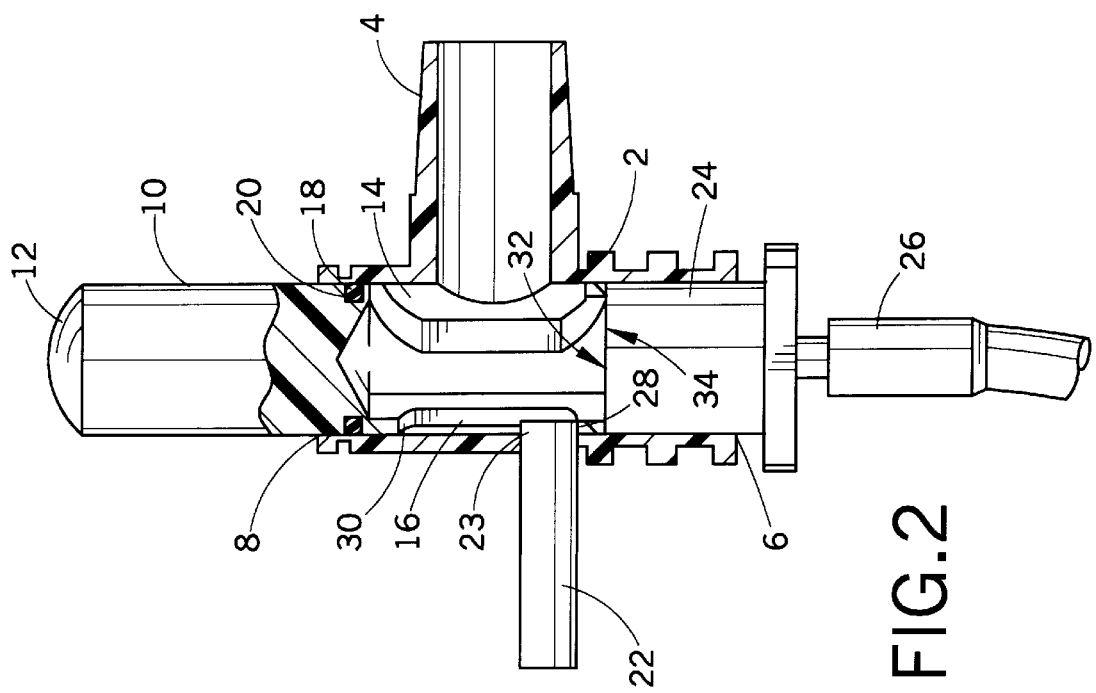
FIG. 2
FIG. 3

ONE HAND DISCONNECTABLE DEVICE FOR ARTIFICIAL BREATHING APPARATUS TO ENDOTRACHEAL TUBE CONNECTIONS

BACKGROUND OF THE INVENTION

1. Field of the Invention

This invention relates to the medical field to fittings and connections between endotracheal tubes and artificial breathing devices such as respirators, ventilators, and the like, and more particularly to a safe one hand disconnect fitting for connection between an endotracheal tube and an artificial breathing device.

2. Description of Related Art

During general anesthesiology a patient must be provided with artificial techniques for breathing because the diaphragm and muscles controlling breathing do not function. Typically, the patient is intubated and an endotracheal tube is inserted. The proximal end of the endotracheal tube is connected to an artificial breathing apparatus. The artificial breathing apparatus can be any device to assist the patient to breathe including automatic and manually operated respirators, ventilators, and the like. (Hereinafter collectively referred to as ventilator(s)).

The connection between the endotracheal tube and the ventilator output tube heretofore been accomplished by the mating together of plastic tubes. A problem associated with the connection between the endotracheal tube and ventilator output tube is disconnection of the ventilator requires using both hands to pull the plastic to plastic connection apart. This results in loss of the sterile environment of both hands of the person disconnecting the ventilator from the endotracheal tube. In addition, the force used to disconnect the tubes can lead to accidental extubation. However, if the ventilator could be removed by one hand, then the other hand could remain sterile, and the danger of accidental extubation eliminated.

SUMMARY OF THE INVENTION

A quick disconnect fitting for connection of a endotracheal tube and a ventilator output tube, that is operable with one hand is provided. The fitting is preferably a rigid body member having an air passage that connects together a ventilator input member and an endotracheal output member. The fitting includes a movable piston or plunger for manual extraction of the endotracheal tube from the endotracheal output member. A finger support member can be provided to grip with at least one finger to obtain leverage to depress the plunger with the palm of a user's hand.

The fitting can include a somewhat "elbow" shaped air passage connectable between the endotracheal tube and the ventilator with a plunger mounted within the air passage to manually disconnect the endotracheal tube by pressure from one hand.

In one embodiment, the fitting is a somewhat "T" shaped hollow rigid body member, with the T vertical shaft representing the ventilator input member, one of the "T" horizontal arms representing the endotracheal output member, the opposite horizontal arm representing the plunger input member into which the plunger is received. The finger support member can be opposite the ventilator input fitting, and if represented, would be a vertical protrusion on the "T" shape.

The ventilator input member receives a rigid connector, which can be plastic, from the ventilator output. The endotracheal output member is sized to receive a rigid connector that is attached by flexible connection tubing to the proximal end of the endotracheal tube. The rigid connector is inserted within the endotracheal output member.

The plunger is received into the plunger input member which is opposite the endotracheal output member. The plunger is slidable within the plunger input member from a first position to a second position. When depressed from the first position, the plunger contacts the rigid connector attached to the endotracheal tube connection tube. With pressure manually provided against the enclosed end of the plunger, the rigid connector is ejected from the endotracheal output member as the plunger moves into the second position. When the rigid connector is inserted into the endotracheal output member, the plunger is pushed back into the first position.

When the plunger is in the first position, and the ventilator output tube and endotracheal tube are connected to the rigid body member, the ventilator is always in fluid communication with the endotracheal tube. The plunger includes an enclosed end cap, and can include at least one aperture or open portion to connect the ventilator input member to the endotracheal output member. A seal can be provided around the plunger to prevent air from escaping from the ventilator through the space between the plunger and the plunger input member, or a flexible boot can be applied over the top of the plunger and sealed to the main body.

The pressure required to depress the plunger from the first position to the second position can be applied with one hand of an operator. However, to provide additional leverage, a rigid finger support member can be placed on the body member opposite the ventilator input member for an operator to grip with at least one finger. The finger support member can further protrude into the hollow interior of the rigid body member to provide a guide and stop for the slidable plunger. The plunger can include a second aperture or slot-like open area that is sized and shaped to receive the interior portion of the finger support member to guide the plunger and retain the plunger within the plunger input member.

Accordingly, it is an objective of the present invention to provide a disconnect for one hand removal of an artificial breathing device from an endotracheal tube.

In accordance with these and other objects which will become apparent hereinafter, the instant invention will now be described with particular reference to the accompanying drawings.

BRIEF DESCRIPTION OF THE DRAWINGS

FIG. 2 is a side elevational view, partially cut away, of the present invention in a first position.

FIG. 3 is a side elevational view, partially cut away, of the present invention in a second position.

DESCRIPTION OF THE PREFERRED EMBODIMENTS

Figure 1:
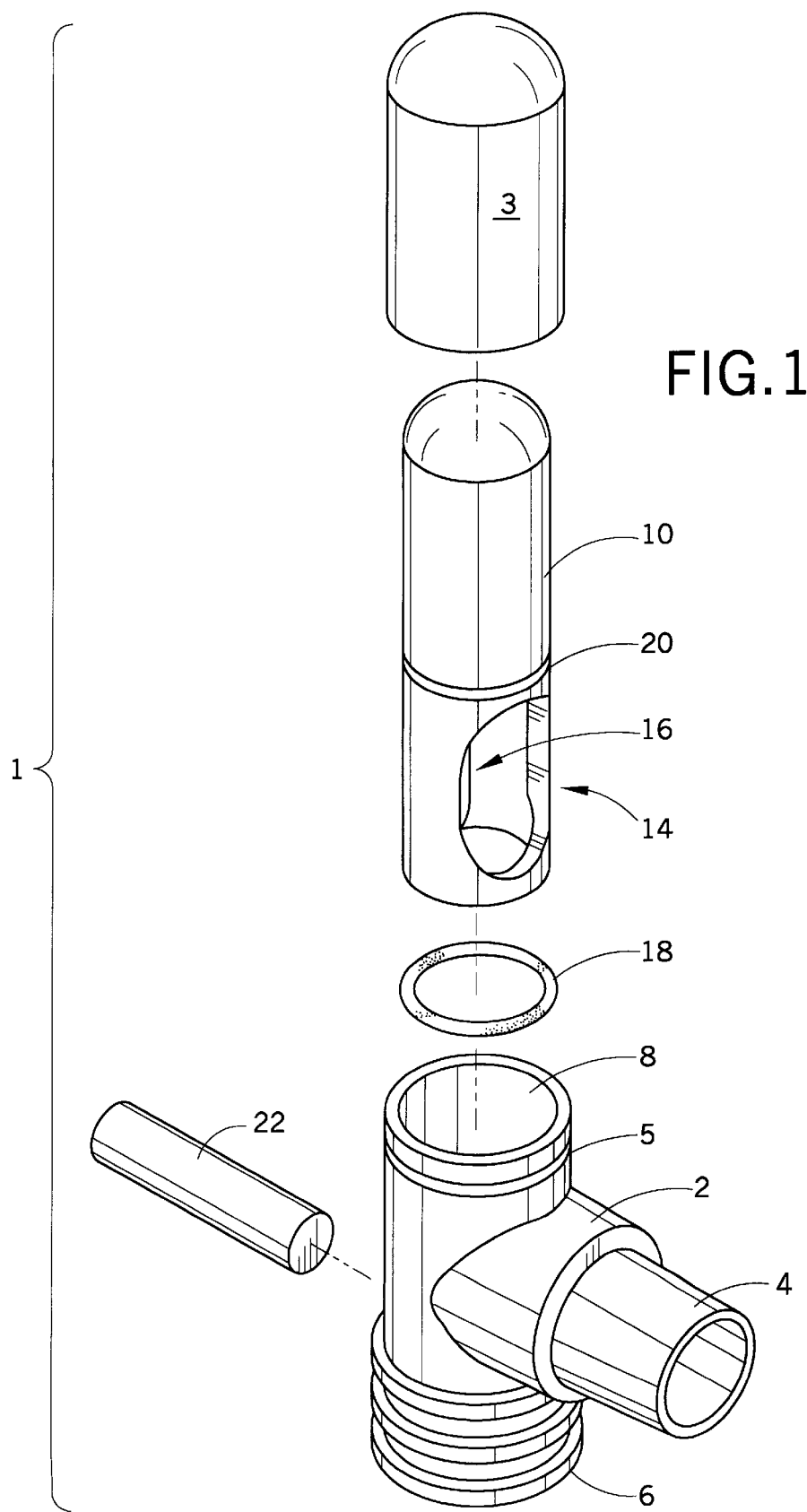
FIG. 1 is an exploded perspective view of the present invention.

FIG. 1 illustrates the preferred embodiment of the present invention generally as 1, comprising hollow rigid body member 2 having ventilator input member 4, endotracheal output member 6, plunger input member 8, and plunger 10. Plunger 10 can be an essentially at least partially hollow cylinder that is sized to slidably fit into plunger input member 8, and includes enclosed end cap 12, aperture 14, and aperture 16. Seal 18 can be placed around plunger 10 and held in recessed area 20. Finger support member 22 can be attached to body member 2.

Referring to FIG. 2, ventilator input member 4 is connectable to a ventilator output tube (not shown). Endotracheal output member 6 receives rigid fitting 24 which is connected to tube 26 which is the proximal end of the endotracheal tube in the patient (not shown). Alternately, tube 26 can be a flexible connection tube that is connected, at the distal end, to the proximal end of the endotracheal tube in the patient. Respiration air travels from the ventilator to the ventilator input member 4, through aperture 14 into the hollow interior portion of plunger 10, through endotracheal output member 6, through rigid fitting 24 to tube 26 and to the endotracheal tube in the patient, and back from the patient through the same airway passage to the ventilator.

Finger support member 22 can be attached to body member 2 such that a portion 23 protrudes into the hollow interior of body member 2. Plunger 10 can include a slot-like aperture 16, opposite aperture 14, that is shaped to receive portion 23 to maintain the rotational position of plunger 10 so that aperture 14 always points toward ventilator input member 4, and maintains the open airway passage from the ventilator to the endotracheal tube.

Portion 23 also serves to prevent plunger 10 from being slid too far out or too far into body member 2 by the lower end 28 and upper end 30 of aperture 14, respectively, contacting portion 23. Finger support member 22 can be removable to permit removal of plunger 10 from body member 2.

Respirator air is prevented from escaping through the space between plunger 10 and plunger input member 8 by seal 18, which can be a conventional shaft seal, and which is held in place by recessed area 20 circumferentially around plunger 10. Alternately, flexible boot 3 can be applied over plunger 10 and sealed by means of recess 5 on rigid body 2, as shown in FIG. 1.

In operation, when rigid fitting 24 is manually inserted into endotracheal output member 6, the upper portion 34 of rigid fitting 24 pushes into the lower portion 32 of plunger 10, and plunger 10 is pushed into a first position as shown in FIG. 2. Rigid fitting 24 fits snugly into endotracheal output member 6 to form an essentially air tight connection.

Referring to FIG. 3, when plunger 10 is pushed in the direction of the arrow, the lower portion 32 of plunger 10 pushes against the upper portion 34 of rigid fitting 24. Continued pressure on plunger 10 results in plunger 10 moving to a second position and fitting 24 being ejected from endotracheal output member 6 and body member 2, as illustrated in FIG. 3.

The ejection of rigid fitting 24 and, hence the connection to the endotracheal tube within the patient, can be accomplished with one hand of an operator. The palm of the hand can be placed against the enclosed end cap 12 of plunger 10 and leverage can be obtained by utilizing ventilator input member 4, which can be gripped by the fingers of the hand. While the use of ventilator input member 4 may provide sufficient leverage to eject fitting 24, finger support member 22 can be provided to grip, with at least one finger, to provide additional leverage. In this manner, only one hand need be used to detach the patient from the ventilator.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A one hand disconnectable fitting having an air passage, comprising:

a rigid and hollow body member comprising:

a first end and a second end located opposite said first end;

an axial bore extending between said first end and said second end;

a plunger input member having a first opening, said plunger input member located at said first end;

an endotracheal output member having a second opening, said endotracheal output member located at said second end;

an artificial breathing apparatus input member having a third opening, said artificial breathing apparatus input member located on said body member between said first and second ends;

wherein a rigid portion of an endotracheal tube is removably connectable to said second opening of said endotracheal output member;

wherein an artificial breathing apparatus is removably connectable to said third opening of said artificial breathing apparatus input member;

a cylindrical, hollow plunger connectable to said one-hand disconnectable fitting slidably received by said first opening of said plunger input member, said plunger connects and disconnects the endotracheal tube from said second opening, wherein said plunger has an enclosed user engagement end and an open disconnection end opposite said enclosed user engagement end, and wherein said plunger is movable to a first position by manual connection of the endotracheal tube and is manually moved to a second position for disconnection of the endotracheal tube by force applied to said enclosed user engagement end;

said plunger having a first aperture to maintain an open airway passage from the artificial breathing apparatus to the endotracheal tube;

a finger support member connectable to said one-hand disconnectable fitting selectively received by an aperture in said body member between said first end and said second end, a portion of said finger support member protruding within said body member through said aperture; and wherein said plunger further includes an elongated slot to receive said portion of said finger support member within said body member and to prevent said plunger from rotational movement and to prevent said plunger from movement beyond said first position or beyond said second position.

2. The device of claim 1 wherein said first aperture of said plunger is elongated so that the third opening to the artificial breathing apparatus remains unobstructed as the plunger moves between first and second positions.

3. The device of claim 1 wherein said artificial breathing apparatus input member is approximately normal to said axial bore of said body member.

4. The device of claim 3 wherein said finger support member is approximately normal to said axial bore of said body member and located opposite said artificial breathing apparatus input member.

5. The device of claim 1 wherein said finger support member is removable from said body member and said plunger is removable from said body member.

6. The device of claim 1 wherein said plunger includes a recess on an exterior surface, and a seal disposed circumferentially within said recessed area, said seal matingly engages an interior surface of said plunger input member to form an air-tight seal between said plunger and said plunger input member.

7. The device of claim 1 further including a flexible housing which slidably engages said plunger and is circumferentially attached to a recessed area of an exterior surface of said plunger input member to form an air-tight seal between said plunger and said plunger input member.

8. A one hand disconnectable fitting having an air passage, comprising:
- a rigid body member having a first end with a first opening, a second end with a second opening, an axial bore extending from said first end to said second end, and an extended portion approximately normal to said rigid body member and located between said first end and said second end, said extended portion having an aperture extending from said axial bore to a third opening of said extended portion; wherein said extended portion selectively receives an artificial breathing apparatus;
- wherein said second opening of said second end of said rigid body member selectively receives an endotracheal tube;
- an elongated cylindrical plunger connectable to said one-hand disconnectable fitting which is slidably received by said first opening of said first end, said plunger connects and disconnects the endotracheal tube from said second opening, said plunger has an enclosed user engagement end which extends exterior to said rigid body member and a hollow portion which extends from an open disconnection end opposite said enclosed user engagement end, said plunger manually movable between a first position and a second position, said plunger having a first elongated aperture to provide an open airway between said aperture of extended portion to said second opening of said body member as said plunger moves from said first position to said second position, said plunger further includes a second aperture opposite said first aperture.

9. The device of claim 8 wherein manual connection of the endotracheal tube into said second opening of said second end of said rigid body member pushes said plunger into said first position.

10. The device of claim 8 wherein said rigid body member further includes a rigid support member approximately normal to and extending outwardly from said axial bore opposite said extended portion, said rigid support member having a portion extending into said axial bore and into said second aperture in said plunger.

11. The device of claim 10 wherein said rigid support member and said plunger are removable.

12. The device of claim 8 wherein said plunger includes a seal disposed circumferentially around said plunger to seal against said axial bore to form an airtight seal between said plunger and said axial bore.

13. The device of claim 8 further including a flexible housing connected to said rigid body member and extending over said plunger to form an air-tight seal between said plunger and said axial bore.

14. A fitting having an air passage, comprising:
- a tube defining an air passage with first, second and third openings, said second opening selectively receives an endotracheal tube, said third opening selectively receives an artificial breathing apparatus, said third opening approximately normal to said tube and located between said first and second openings, said second opening opposite said first opening;
- a plunger connected to said fitting, said plunger mounted in said tube through said first opening for connecting and disconnecting the endotracheal tube from said second opening, wherein said plunger has an enclosed user engagement end and an open disconnection end opposite said enclosed user engagement end and wherein said plunger is movable between a first position by manual connection of the endotracheal tube and is manually moved to a second position for disconnection of the endotracheal tube by force applied to the enclosed user engagement end; and
- a finger support member connectable to said fitting, said finger support member located opposite said third opening within an aperture in said tube.

15. The device of claim 14 wherein said plunger further includes a first aperture which provides an open airway between said second and third openings, and a second aperture into which extends a portion of said finger support member.

* * * * *